United States Patent
Kishida et al.

[11] Patent Number: 5,928,658
[45] Date of Patent: Jul. 27, 1999

[54] OIL-FREE WAX-FREE SOLID COSMETIC COMPOSITION

[75] Inventors: Shigeru Kishida, Storrs; William Zavadoski, Madison; Masaru Kobayashi, Woodstock, all of Conn.

[73] Assignee: U.S. Cosmetics, Dayville, Conn.

[21] Appl. No.: 08/985,805

[22] Filed: Dec. 5, 1997

[51] Int. Cl.⁶ .............................. A91K 7/00; A91K 7/035; A91K 9/14; A91K 9/16
[52] U.S. Cl. ............................ 424/401; 424/69; 424/489; 424/490; 424/642; 424/646; 424/682; 514/78; 514/770; 514/773
[58] Field of Search ..................................... 424/401, 489, 424/490, 69, 642, 646, 682; 514/78, 770, 773

[56] References Cited

U.S. PATENT DOCUMENTS

| | | | |
|---|---|---|---|
| 4,606,914 | 8/1986 | Miyoshi | 424/63 |
| 4,622,074 | 11/1986 | Miyoshi et al. | 106/308 F |
| 4,863,800 | 9/1989 | Miyoshi et al. | 428/403 |
| 5,030,446 | 7/1991 | Russ et al. | 424/63 |

*Primary Examiner*—Shelley A. Dodson
*Assistant Examiner*—Marina Lamm
*Attorney, Agent, or Firm*—Graham & James LLP

[57] ABSTRACT

An oil-free and wax-free solid or powder-based cosmetic material having beneficial oil and wax characteristics without the detrimental effects thereof. The cosmetic material comprises pigments and/or pigment extenders which are surface treated with a hydrophobizing material to become hydrophobic. The hydrophobidized cosmetic material is admixed with oil-free and wax-free binders in an aqueous slurry and then vacuum dehydrated and dried at an elevated temperature to provide the finished cosmetic product with excellent skin "feel", adhesiveness, extendibility, payoff (i.e., pickup of the product by an applicator) and uniformity characteristic of oil-containing cosmetics but without oil and its detrimental effects.

14 Claims, No Drawings

OIL-FREE WAX-FREE SOLID COSMETIC COMPOSITION

FIELD OF THE INVENTION

This invention relates to solid cosmetic compositions, particularly of the solid or solid like cake type, such as used in make-up preparations.

BACKGROUND OF THE INVENTION

Oils and waxes are usually utilized in solid or cake-like cosmetic products as binder materials in make-up preparations such as face powder, powder foundation, eye shadow, mascara, rouge and the like. Because oils and waxes are slippery, with lubricating properties, cosmetics made therewith produce the positive effects on skin, of a feel of richness and creaminess, though to some users this may feel objectionably greasy. In a negative aspect, in many instances, the oily and waxy materials tend to soil clothing and other items with which they are brought into contact.

Oils are derived from animal, vegetable and mineral sources or they can be synthesized and are generally characterized as being slippery, combustible, viscous, liquid or liquefiable at room temperatures, and are soluble in various organic solvents, such as ether but not in water. Waxes are also derived from animal, vegetable, and mineral sources and can also be synthesized and are generally similar in composition and properties to oil except that waxes contain no glycerides and are generally solid in nature (though in a very viscous form).

In a typical application such as a cake type foundation, oil content (wt. %) ranges from 3 to 15% wherein the oily components are used as binders and to increase creaminess and adhesion to the skin. Anhydrous foundation and emulsion type foundation typically contain 10 to 20% of oil, with increase of oil content serving to increase extendibility and adhesiveness of cosmetic products. However, oil components tend to retard normal physiological functions such as perspiration and respiration through the skin, particularly when the oily components are present in cosmetic products in high percentages.

Dermatological problems may be caused when the oil-containing cosmetic such as a dry skin moisturizer, clogs pores. This condition contributes to the incidence of acne vulgaris, the most common skin disorder. Increased sebum production particularly in teenagers and disturbance of follicular keratinization are believed to be the primary causes of acne. Removal of excess skin oil by frequent washing and cleaning is the most recommended method for the treatment of acne. However, application of additional oil to the face, such as with cosmetics containing high levels of oily components, tends to worsen the acne condition. In addition, use of cosmetics increases the possibility of free radical generation upon exposure to UV, which in turn causes degeneration of oils, resulting in the production of skin irritating lipid peroxide.

The terms "oil-free" and "oil-control" are used in claims made by many marketers of pressed powders. These claims are linked to products which also claim "shine-control", "matte-look", "no more shine" and/or "shine-free", face powders are traditionally used to subdue the "shine" on the faceassociated with the release of sebum (a natural oily/fatty exudate) especially when it is hot and/or humid. Since the consumer expects these powder products to live up to their claims, they should not contain any oil(s) in their formulations.

Another problem when oil is used as a binder in the production of cosmetic products, is that the oil must be uniformly dispersed so that pigments and/or extender pigments do not agglomerate since non-uniformity is problematic in the production of pressed powder cosmetic products.

Oil-free liquid foundations exist. However, oil-free, non-liquid containing, pressed powder cosmetic make-up products do not truly exist. Those non-liquid cosmetic make-up products claiming to be oil-free, commonly contain silicone and/or other similar types of materials which are properly characterized as oils.

SUMMARY OF THE INVENTION

It is an object of the present invention to provide a truly oil-free pressed powder cosmetic make-up product comprised of pigments and/or extender pigments which are surface treated to make them hydrophobic and then mixed with oil-free and wax-free binders and additives, which provides them with desirable oil component characteristics but without oily component drawbacks.

It is a further object of the present invention to surface treat the cosmetic composition with hydrophobidizing agents and to form the cosmetic material with cosmetically acceptable non-oil, non-wax binder materials.

It is still yet a further object of the present invention to effect the surface treatment with one or more of amino acid, metal soap, collagen, and polyethylene, together with the use of dry binders and auxiliary materials, depending upon the specific need.

In accordance with the present invention, the pigments and/or extender pigments are made hydrophobic in an aqueous environment with an agent having a lipophilic moiety, such as water-insoluble metal salts of fatty acids, acylamino acids, hydrogenated lecithin, acyl collagen and the like. Surface treatment agents having suitable lipophilic moieties are described in U.S. Pat. Nos. 4,606,914, 4,623,074 and 4,863,800 and Japanese Patents 60-69011 and 61-73775.

These and other objects, features and advantages of the present invention will become more evident from the following discussion.

DETAILED DESCRIPTION OF THE INVENTION

The oil materials excluded from the cosmetic composition of the present invention are any and all of mineral oil, vegetable oil, animal oil or synthetic oil and similarly the excluded wax is from any of the animal, vegetable, mineral sources or a synthetic type.

Non-oil, non-wax type binders include the stearates and/or oxides of aluminum, calcium, lithium, magnesium, potassium, silicon, sodium, sorbitan, as well as calcium phosphate; natural gums including acacia gum, tragacanth gum, guar gum, locust bean gum and karaya gum; rosin and rosin derivatives; cellulose and cellulose derivatives; starches and starch derivatives; and clay and clay-like materials.

In pending U.S. application Ser. No. 08/658,461, assigned to the present assignee, the described hydrophobidization of the pigments and pigment extenders is similarly effected but for enhanced binding of the oily components. It has been unexpectedly discovered that it is possible to completely eliminate oily components without the loss of the beneficial aspects thereof.

In accordance with the present invention, the cosmetic composition powders of pigments and extender pigments are initially surface treated with one or more hydrophobidizing agents to uniformly coat the particles of the powder. Thereafter, the surface treated powder is mixed with an oil-free, wax-free binder material and water to produce a slurry suspension. The slurry is preferably dried by being back injected into a vessel or container and the injected material is vacuum dehydrated through a filter in the surface of the container, in a procedure and with an injection machine described in U.S. Pat. No. 4,967,810, the disclosure of which is included herein by reference thereto. After dehydration, the resultant product is dried at an elevated temperature for a sufficient time to provide the finished product.

In accordance with the present invention, pigments or extender pigments are made hydrophobic in an aqueous environment with an agent having a lipophilic moiety. Examples of such hydrophobidizing surface treatment materials include water-insoluble metal salts of fatty acids, acylamino acid, hydrogenated lecithin or acyl collagen. The water insoluble salts are preferably salts of polyvalent metal such as magnesium, calcium, aluminum, titanium, zinc or zirconium. An aqueous slurry is formed with the hydrophobidized pigments and/or extender pigments being admixed with suitable oil-free and/or wax-free binders and with optional oil-free and wax-free additives in sufficient water to form a slurry of suitable viscosity.

Suitable fatty acids providing the lipophilic moiety include lauric acid, myristic acid, palmitic acid, oleic acid, stearic acid, isostearic acid, behenic acid and the like. Water-soluble salts of such fatty acids may be formed with sodium, potassium or aluminum.

Suitable acylamino acids include N-acyl-L-glutamic acid, N-acyl-N-methylglycine, N-acyl-N-methyl-β-alanine and the like. The acyl group may include a residue of lauric acid, myristic acid, palmitic acid, oleic acid, stearic acid, isostearic acid, and behenic acid. Water-soluble salts of such acylamino acids may be formed with sodium, potassium or ethanolamine.

Suitable hydrogenated lecithins include (1) hydrogenated natural lecithin obtained by extraction of lecithin from egg yolk, soy bean oil, corn oil, and rapeseed oil followed by hydrogenation; and (2) hydrogenated synthetic lecithin. The iodine value of the hydrogenated lecithin should preferably be less than 30. The term "lecithin" refers to the overall composition; therefore, the lecithin which can be used in the present invention does not have to be pure phosphatidyl choline, but may contain other phospholipids and neutral fats in addition to phosphatidyl choline. Water-soluble salts of the hydrogenated lecithins may be formed with sodium or potassium.

Suitable acyl collagens include those obtained by acylation of an oligopeptide or peptide. Useful oligopeptides or peptides are obtained by partially hydrolyzing protein and/or collagen and have n=1–100. The acyl group may include a residue of lauric acid, myristic acid, palmitic acid, oleic acid, stearic acid, isostearic acid, and behenic acid. Water-soluble salts of such acyl collagens may be formed with sodium or potassium.

The water-soluble salts having a lipophilic moiety used in the present invention are soluble at room temperature or in warm water. When one or more of these salts are added to the pigments and/or extender pigments the lipophilic moiety is adsorbed on the surface of the pigment and/or extender pigment particles. In order to complete the adsorption of the lipophilic moiety, an aqueous solution of a water soluble polyvalent metal salt, such as 1–30% by weight aqueous solution of a water-soluble salt of Al, Mg, Ca, Zn, Zr, or Ti, is added in sufficient amount to give a proportion of 1–2 equivalents of the polyvalent metal salt of the fatty acid, acylamino acid, hydrogenated lecithin, or acyl collagen and the like. Useful water-soluble, polyvalent metal salts include aluminum sulfate, aluminum chloride, aluminum nitrate, aluminum potassium sulfate, magnesium sulfate, magnesium chloride, magnesium nitrate, magnesium potassium sulfate, calcium chloride, calcium nitrate, calcium acetate, zinc sulfate, zinc chloride, zinc nitrate, zinc acetate, zirconium sulfate, zirconium chloride, titanium oxysulfate, and titanium chloride. The polyvalent metal salt reacts with the salt of the fatty acid, acylamino acid, hydrogenated lecithin, acyl collagen and the like to form a water-insoluble reaction product which becomes chemically bound onto the surface of the pigment and extender pigment particles.

In a preferred embodiment of the invention, the aqueous slurry consists essentially of from about 10 to about 50% by weight of water, from about 40 to about 70% by weight of the particles of hydrophobic pigments and extender pigments and from about 1 to about 30% by weight of the oil-free and wax-free binders and additives.

The amount of the surface-treating agent used in the present invention is dependent upon the particle size or specific surface area of the pigments or extender pigments being treated. Suitably, the amount of the surface-treating agent is from about 1 to about 20% by weight based on weight of the pigments, preferably from about 2 to about 5% by weight.

The amounts of the oil-free and wax-free components range from about 1 to about 30% by weight of the pigments or extender pigments, and preferably from about 2 to about 15% by weight.

The pigments or extender pigments used in the present invention include organic and inorganic pigments, such as titanium dioxide, zinc oxide, zirconium dioxide, yellow iron oxides, black iron oxides, red iron oxides, ultramarine blues, Prussian blues, chromium oxides, chromic hydroxides, and the like, pearlescent pigments, such as mica coated with titanium dioxide, bismuth oxychloride, coal-tar pigments, natural pigments, silica beads, nylon beads, acrylic beads, talc, kaolin, mica-like minerals, such as sericite type materials, magnesium carbonate, calcium carbonate, aluminum silicate, magnesium silicate, calcium silicate and clay and the like.

In addition to containing pigments and extender pigments as described above, oil-free and wax-free molding additives may be included depending on the need, to further improve the product quality. These molding additives may be natural cellulose powder, metal soaps, e.g., metallic stearates, calcium phosphates and like materials used in molding cosmetics or pharmaceuticals.

In order to illustrate the effectiveness of the present invention, the following example illustrates the preparation of a cosmetic preparation without oil or wax components. It is understood that details contained therein are not to be construed as limitations on the present invention.

EXAMPLE 1 (foundation)

A cosmetic composition of pigments and extender pigments with the following components was mixed together for one minute:

| | |
|---|---|
| mica | 60 parts |
| talc | 40 parts |
| titanium dioxide | 3 parts |
| calcium phosphate | 7 parts |
| brown iron oxide | 5 parts |
| yellow iron oxide | 1 part |
| red iron oxide | 0.5 parts |
| black iron oxide | 0.5 parts |

Sodium myristate, dissolved in 50 ml of water and heated to 80° C. was added and mixed for 10 minutes. Aluminum chloride in aqueous solution (1.5 equivalents relative to the sodium myristate) was added dropwise to the component mixture whereby the pigments in the mixture were surface treated with the hydrophobidizing aluminum myristate which was formed in situ. To the coated material was added 0.2 g of methylparaben and 0.2 g of butylparaben as non-oil, non-wax preservative materials, with sufficient water for mixing and production of a slurry to be used as a cosmetic foundation. An injection machine, as described above, was used for injection into a vacuum dehydration vessel and the injected material was vacuum dehydrated through a surface filter of the vessel, and dried at 40° C. for 2–12 hours to produce the finished foundation product. When used, the foundation product had excellent skin "feel", adhesiveness, extendibility, payoff (i.e., pickup of the product by an applicator) and uniformity.

EXAMPLE 2 (eyeshadow)

The following components were mixed for one minute:

| | |
|---|---|
| Talc | 80.0 g |
| Aluminum stearate | 6.0 g |
| Zinc stearate | 6.0 g |
| Ultramarine blue | 5.4 g |
| Black iron oxide | 0.1 g |
| Chromium hydroxide green | 2.0 g |
| Yellow iron oxide | 0.5 g |

Sodium myristate, dissolved in 50 ml of water and heated to 78° C. was added to the above and mixed for 5 minutes. Aluminum chloride aqueous solution was added and further mixed. To the mixture 0.3 g of silver borosilicate was added with sufficient water for mixing and production of a slurry to be used as a cosmetic eyeshadow. A injection machine was used for injection into a vessel and the injected material was dried at room temperature for 8–16 hours to produce the finished eyeshadow product. The eyeshadow exhibited superior long lasting qualities.

EXAMPLE 2 (blush)

The following components were mixed for three minutes:

| | |
|---|---|
| Sericite | 40.0 g |
| Talc | 25.0 g |
| Mica | 10.0 g |
| Kaolin | 5.0 g |
| Aluminum stearate | 6.0 g |
| Red iron oxide | 4.5 g |
| Black iron oxide | 0.1 g |
| Brown iron oxide | 8.0 g |
| Yellow iron oxide | 0.2 g |
| Titanium dioxide | 4.0 g |

To the mixture, 3.2 g of locust bean gum, dispersed in 50 ml water, was added and throughly mixed. Sodium myristate, dissolved in 50 ml of water and heated to 70° C. was added to the above and mixed for 10 minutes. Aluminum chloride aqueous solution was added slowly and mixed until homogeneous. To the mixture 0.2 g of silver borosilicate and 0.1 g of methylparaben were added with sufficient water for mixing and production of a slurry to be used as a cosmetic cake blusher. A back injection machine was used for injection into a vessel and the injected material was dried at room 50° C. for approximately 10 hours to produce the finished cheek blusher product. The blusher was easy to apply to the cheek area. It lasted for a long time on the cheeks with true color.

It is understood that the above specific examples are merely illustrative of the present invention and that changes may be made to the composition, relative ingredient ratios and types of makeup, and the like, without departing from the scope of the present invention as defined in the following claims.

What is claimed is:

1. An oil-free, wax-free solid cosmetic composition comprising particles of at least one cosmetic pigment and pigment extender and a cosmetically acceptable oil-free and wax-free binder wherein the surfaces of the particles of the at least one cosmetic pigment and extender pigment are hydrophobidized with a hydrophobidizing agent prior to admixture of the at least one cosmetic pigment and extender pigment with the oil-free and wax-free binder, in an aqueous slurry, and wherein the slurry is vacuum dehydrated and dried to provide said composition.

2. The cosmetic composition of claim 1, wherein the hydrophobidizing agent is selected from the group consisting of amino acid, metal soap, collagen, and polyethylene.

3. The cosmetic composition of claim 1, wherein the surfaces of the at least one pigment and extender pigment are made hydrophobic in an aqueous environment with an agent having a lipophilic moiety, selected from the group consisting of water-insoluble metal salts of fatty acids, acylamino acids, hydrogenated lecithin, and acyl collagen.

4. The cosmetic composition of claim 3, wherein the fatty acids having the lipophilic moiety are selected from the group consisting of lauric acid, myristic acid, palmitic acid, oleic acid, stearic acid, isostearic acid, behenic acid and the water-soluble salts thereof are formed with sodium, potassium, or aluminum.

5. The cosmetic composition of claim 3, wherein the acylamino acids are selected from the group consisting of N-acyl-L-glutamic acid, N-acyl-N-methylglycine, and N-acyl-N-methyl-β-alanine.

6. The cosmetic composition of claim 3, wherein an acyl group of the acyl amino acid is comprised of at least one of a residue of lauric acid, myristic acid, palmitic acid, oleic acid, stearic acid, isostearic acid, and behenic acid and wherein the water-soluble salts of the acylamino acids are formed with one of aluminum, sodium, potassium and ethanolamine.

7. The cosmetic composition of claim 3, wherein the hydrogenated lecithin is selected from the group consisting of (1) hydrogenated natural lecithin obtained by extraction of lecithin from egg yolk, soy bean oil, corn oil, and rapeseed oil followed by hydrogenation; and (2) hydrogenated synthetic lecithin, wherein the iodine value of the hydrogenated lecithin is less than 30 and wherein water-soluble salts of the hydrogenated lecithins are formed with sodium, potassium, or aluminum.

8. The cosmetic composition of claim 3, wherein the acyl collagens comprise those obtained by acylation of one of an oligopeptide and a peptide and wherein the oligopeptides and peptides are obtained by partially hydrolyzing protein and/or collagen and have n=1–100 and wherein the acyl group of the acyl collagen includes one of a residue of lauric acid, myristic acid, palmitic acid, oleic acid, stearic acid, isostearic acid, and behenic acid and wherein water-soluble salts of the acyl collagens are formed with sodium, potassium, or aluminum.

9. The cosmetic composition of claim 1, wherein the binder is selected from the group consisting of stearates and oxides of aluminum, calcium, lithium, magnesium, potassium, silicon, sodium, sorbitan; calcium phosphate; natural gums; rosin; and cellulose.

10. The cosmetic composition of claim 1, wherein the pigments and extender pigments comprise organic and inorganic pigments, selected from the group consisting of titanium dioxide, zinc oxide, zirconium dioxide, yellow iron oxides, black iron oxides, brown iron oxides, red iron oxides, ultramarine blues, Prussian blues, chromium oxides, chromic hydroxides, pearlescent pigments, mica coated with titanium dioxide, bismuth oxychloride, coal-tar pigments, natural pigments, silica beads, nylon beads, acrylic beads, talc, kaolin, mica, sericite, magnesium carbonate, calcium carbonate, aluminum silicate, magnesium silicate, calcium silicate and clay.

11. The cosmetic composition of claim 10, wherein the cosmetic is foundation.

12. The cosmetic composition of claim 10, wherein the cosmetic is eyeshadow.

13. The cosmetic composition of claim 10, wherein the cosmetic is blush.

14. A method for the preparation of oil-free and wax-free solid cosmetic compositions comprising the steps of:

a) uniformly hydrophobidizing the surface of particles of pigments and extender pigments used in said cosmetic composition to render such surfaces hydrophobic;

b) admixing the hydrophobidized particles with a cosmetically acceptable oil-free, wax-free binder in an aqueous slurry; and c) vacuum dehydrating the slurry and drying at an elevated temperature to provide the cosmetic composition.

* * * * *